US012618086B2

(12) United States Patent
Gabelle et al.

(10) Patent No.: US 12,618,086 B2
(45) Date of Patent: May 5, 2026

(54) METHOD FOR PRODUCING ALCOHOLS USING A SUPPORT ON WHICH MICROORGANISMS ARE IMMOBILISED

(71) Applicant: IFP Energies nouvelles, Rueil-Malmaison (FR)

(72) Inventors: Jean-Christophe Gabelle, Rueil-Malmaison (FR); Eszter Toth, Rueil-Malmaison (FR); Nicolas Lopes Ferreira, Rueil-Malmaison (FR); Helene Velly, Rueil-Malmaison (FR); Amandine Ginet, Rueil-Malmaison (FR); Severine Artero, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 322 days.

(21) Appl. No.: 18/267,625

(22) PCT Filed: Dec. 2, 2021

(86) PCT No.: PCT/EP2021/083876
§ 371 (c)(1),
(2) Date: Jun. 15, 2023

(87) PCT Pub. No.: WO2022/128492
PCT Pub. Date: Jun. 23, 2022

(65) Prior Publication Data
US 2024/0060095 A1 Feb. 22, 2024

(30) Foreign Application Priority Data
Dec. 18, 2020 (FR) ...................................... 2013608

(51) Int. Cl.
*C12P 7/16* (2006.01)
*C12N 11/02* (2006.01)
*C12P 7/06* (2006.01)
*C12R 1/145* (2006.01)

(52) U.S. Cl.
CPC ............... *C12P 7/16* (2013.01); *C12N 11/02* (2013.01); *C12P 7/065* (2013.01); *C12R 2001/145* (2021.05)

(58) Field of Classification Search
CPC . C12P 7/16; C12P 7/065; C12N 11/02; C12N 11/08; C12R 2001/145; Y02E 50/10; C12M 21/12; C12M 25/18
See application file for complete search history.

(56) References Cited

U.S. PATENT DOCUMENTS

| | | | |
|---|---|---|---|
| 4,524,139 A | 6/1985 | Fuchs | |
| 5,079,011 A | 1/1992 | Lommi et al. | |
| 11,453,853 B2 * | 9/2022 | Gonzalez Penas | ....... B08B 3/08 |
| 2021/0340480 A1 * | 11/2021 | Gonzalez Penas | .. C12N 11/093 |

FOREIGN PATENT DOCUMENTS

| | | | |
|---|---|---|---|
| EP | 0361165 A1 | 4/1990 | |
| FR | 2550220 A1 | 2/1985 | |
| WO | 2020064900 A1 | 4/2020 | |
| WO | 2020064901 A1 | 4/2020 | |

OTHER PUBLICATIONS

Bankar et al., Butanol: the outlook of an academic and industrialist. RSC Adv., 2013, vol. 3: 24734-24757. (Year: 2013).*
Mate de Gerando., Improving isopropanol tolerance and production of Clostridium beijerinckii DSM 6423 by random mutagenesis and genome shuffling. Appl Microbiol Biotechnol., 2016, vol. 100: 5427-5436 (Year: 2016).*
Radovich JM., Mass Transfer Limitations in Immobilized Cells. Biotech Advs., 1985, vol. 3: 1-12 (Year: 1985).*
International Search report PCT/EP2021/ 083876 dated Feb. 14, 2022 (pp. 1-3).

* cited by examiner

*Primary Examiner* — Ganapathirama Raghu
(74) *Attorney, Agent, or Firm* — Millen, White, Zelano & Branigan, P.C.; Jennifer L. King

(57) ABSTRACT
The present invention relates to a process for producing alcohols, according to which a sugary fluid (2) is introduced into a reaction section (1) comprising a support (4) on which microorganisms are immobilized, in order to produce, by fermentation, an alcohol-enriched must (3) under the action of said microorganisms, characterized in that the process is carried out continuously, and such that a portion of spent support (41) is periodically replaced by a portion of new and/or regenerated support (46).

20 Claims, 3 Drawing Sheets

METHOD FOR PRODUCING ALCOHOLS USING A SUPPORT ON WHICH MICROORGANISMS ARE IMMOBILISED

TECHNICAL FIELD

The present invention relates to a process for producing alcohols by fermentation of a sugary fluid.

PRIOR ART

In order to meet the energy transition challenges, considerable research is being conducted to develop "green" processes, affording access to chemical intermediates in an alternative manner to petroleum refining and/or petrochemistry.

Alcohols derived from fermentation processes (for example isopropanol and n-butanol) are among the most promising replacements for petrochemical derivatives. ABE (Acetone—Butanol—Ethanol) fermentation, performed by microorganisms belonging to the genus *Clostridium*, is one of the oldest fermentations to have been industrialized, and has since been extensively studied. More recently, IBE (Isopropanol—Butanol—Ethanol) fermentation, producing a mixture of isopropanol, butanol and ethanol and also performed by microorganisms belonging to the genus *Clostridium*, has been the subject of numerous studies.

As regards the fermentation approach employed in this type of process, batch production remains the conventional method for ABE and IBE fermentations, despite the low productivity displayed for this type of process, in the range 0.1-0.7 g/L·h (see, for example, Jones D. T., Woods D. R., 1986, Acetone-Butanol Fermentation Revisited. Microbiol. Rew., 50 (4), 484-524 or Table 16.6 Lopez-Contreras A. et al. chapter book 16, Bioalcohol Production: Biochemical Conversion of Lignocellulosic Biomass, 2010). However, these productivities remain too low to envisage an economically viable industrial process.

A continuous process with cells in suspension in a homogeneous reactor may also be envisaged. However, the productivity is also relatively low and cannot easily be significantly increased. One technical problem is the concentration of the cells in the fermentation medium, which is mainly controlled by the dilution rate applied in the process. This rate cannot be high, to avoid cell "wash-out" in the fermenter. For these reasons, great interest has been shown in recent years in methods directed toward high retention of the microbial biomass. Two means exist: "immobilization of the cells" and cell "recycling" with retention by means of membrane filters. The present invention will mainly focus on the cell immobilization technique.

Two immobilization techniques for the continuous process are known: adsorption on a solid support and entrapment, the two techniques having been studied in the literature for ABE production.

In the first case of adsorption on a solid support, the physical adsorption of microorganisms onto a solid surface takes place via electrostatic forces, van der Waals forces, or by covalent bonding between the bacterial cell membrane and the support. As there is no physical barrier between the microbial biofilm and the fermentation solution, various equilibria between the degrees of adsorption, of cell detachment and of recolonization of the solid support may be achieved as a function of the solid support, of the implementation and of the operating conditions. It should be noted that the immobilized cells are typically surrounded by polysaccharides excreted by the microorganisms (EPS:

"Extracellular Polymeric Substances"), and have different growth and bioactivity regimes from those obtained when the cells are in suspension (see, for example, Halan B., Buehler K., Schmid A., 2012, Biofilms as living catalysts in continuous chemical syntheses, Trends in Biotechnol., 30 (9), 453-465).

Several solid supports have been tested and prove to be advantageous according to the literature for ABE fermentation, including charcoal (see, for example, Qureshi N., Maddox I. S., 1987, Continuous solvent production from whey permeate using cells of *Clostridium acetobutylicum* immobilized by adsorption onto bonechar, Enzyme Microb. Technol., (9), 668-371), bricks (see, for example, Qureshi N., Schripsema J., Lienhardt J., Blaschek H. P., 2000, Continuous solvent production by *Clostridium beijerinckii* BA101 immobilized by adsorption onto brick, World Journal of Microbiology & Biotechnology, (16), 377-382), and paper pulp (see, for example, Survase S. A., van Heiningen A., Granström T., 2012, Continuous bio-catalytic conversion of sugar mixture to acetone-butanol-ethanol by immobilized *Clostridium acetobutylicum* DSM 792, Appl. Microbiol. Biotechnol., (93), 2309-2316). But such solid supports are not synthetic and may give rise to major problems of reproducibility for fermentation processes.

In the second case, that of immobilization by entrapment, of encapsulation type, the microorganisms are introduced inside a porous matrix, so as to prevent their diffusion into the external medium, while at the same time allowing the transfer of material for the support and the nutrients, and also for the reaction products. Examples of supports using the encapsulation entrapment technique include alginate beads (see, for example, Mollah A. H., Stuckey D. C., 1993, Maximizing the production of acetone-butanol in alginate bead fluidized bed reactor using *Clostridium acetobutylicum*, J. Chem. Tech. Tech. Biotechnol., (56), 83-89), and k-carrageenan beads (see, for example, Godia F., Howard I., Scott D., Davison B. H., 1990, Use of immobilized microbial membrane fragments to remove oxygen and favor the acetone-butanol fermentation, Biotechnol. Prog., 1990, 210-213).

A process has furthermore been proposed in patent FR-3 086 670 in which at least one portion of the bacterial biomass is fixed in the fermentation reactor by adsorption in the form of a biofilm on a porous material based on polymeric foam, of polyurethane foam type. This material has proven to be particularly efficient, allowing a continuous fermentation process, the foam making it possible to fix the bacteria in a sufficiently substantial manner, i.e. beyond the dilution rate causing cell wash-out. This material opens up a new pathway for the production of mixtures of IBEA type, while also giving access to a production in continuous mode by immobilization of the bacterial biomass.

Patent FR-3 086 553, moreover, proposes a process for cleaning this polyurethane foam, consisting in bringing the foam into contact with a fluid originating from a fermentation must enriched in alcohol and/or acetone and/or an aqueous solution at basic pH. It is thus possible, once the polymeric foam is "spent", in particular clogged and/or saturated with biomass, to regenerate it by cleaning in order to reuse it in a fermentation reactor with a performance identical to or similar to that of a new foam.

However, continuous production processes of this type, with immobilization of the microorganisms on a support in the fermentation reactor, remain susceptible to improvement, in particular because they require transient phases, ramp-ups of the cell immobilization on the supports, and phases of regular replacement of the supports, long phases which are detrimental to their productivity.

The objective of the invention is thus to improve continuous fermentation processes, of the type of those producing mixtures of ABE or IBE alcohols, in particular with a view to improving their productivity.

SUMMARY OF THE INVENTION

The invention firstly relates to a process for producing alcohols, according to which a sugary fluid is introduced into a reaction section comprising a support on which microorganisms are immobilized, in order to produce, by fermentation, an alcohol-enriched must under the action of said microorganisms, such that the process is carried out continuously, and such that one portion (only) of spent support is periodically replaced by a portion of new and/or regenerated support.

In the context of the invention, a "spent" support is understood to mean a support whose performance is reduced compared to a new support, in particular by reaching a given clogging/saturation threshold level, or by reaching a given production lifespan. The support will generally be even more spent when it is "old", i.e. when it has been used for a certain time from the start-up to a given instant of a production run.

In the context of the invention, a "regenerated" support is understood to mean a spent support which has been treated/cleaned in order to once again achieve a performance similar to or identical to a "new" support.

In the context of the invention, a "new" support is understood to mean a support which has never before been used in production, and which has therefore not yet been colonized by microorganisms.

The invention therefore relates to continuous fermentation processes, with a support immobilizing the microorganisms in a fermentation reactor. As briefly mentioned above, these supports, a bit like catalysts in the field of chemistry, are gradually deactivated: The support is colonized with microorganisms (bacteria) at the start, then the support becomes loaded with bacteria over time. This accumulation is beneficial for a certain period of time, since it increases the concentration of bacterial biomass, and it therefore increases the volume productivity of the fermentation reactor. But beyond a certain period of time, the support is fully colonized by bacteria, and clogging phenomena appear: when the support material is in the form of blocks or particles, clogging can be observed between the particles/blocks and/or within the particles/blocks when the material thereof is porous, which then causes production to drop. In addition, it is necessary to take into account the mortality of the cells in the biofilm, the deterioration observed therefore being the combination of increasing clogging phenomena and the increasing death of the bacteria over time.

The solution proposed by the invention is to use a support that can be replaced gradually, each time replacing one portion of the support with a new/regenerated portion. The support is thus partially renewed: the portion of new or regenerated support that is introduced is gradually colonized in turn by the bacteria, and gradually becomes effective, more than the spent portion that was removed. With this system, the support maintains a sufficient overall effectiveness throughout the production run, with portions of support that have different "ages". (The "age" is understood to mean the time spent, at time t, by a portion of support in production since the start of a production run): the most spent/ oldest portions of the support are gradually replaced in order to replace them with new/regenerated portions, thus retaining an average "age", average deterioration, which are generally unchanged for the support.

Advantageously, the microorganisms are, according to the invention, immobilized on the support in the form of biofilms or aggregates on/in the support, chosen preferably to be porous.

Advantageously according to the invention, the support comprises a plurality of support portions arranged successively in a general direction of flow of the (sugary) fluid in the reaction section, and said portions have a decreasing degree of deterioration from upstream to downstream (relative to this direction of flow). It is specifically the furthest upstream portion in relation to the stream of sugary liquor which tends to become loaded first with bacteria, which will therefore deteriorate more than the following ones. According to the invention, this fact is therefore exploited to bring about a controlled partial rejuvenation of the support.

Thus, preferably, according to the invention, the portion of spent support which is furthest upstream in the support is replaced by the portion of new or regenerated support which is itself placed downstream of the furthest downstream portion of the support.

The support preferably comprises loose blocks of porous material, which are, in the reaction zone in production, immersed in a liquid reaction medium bathing said reaction section. These blocks are preferably held in the reaction section by mechanical devices, which are meshed, such as screens, nets or plates provided with orifices, and/or in the form of deflectors.

For the purposes of the invention, the term "loose" is understood to mean the fact that the blocks are not arranged relative to one another in an ordered manner.

The support may preferably be made of a material of foam type, either based on a polymer, of polyurethane (PU) foam type, or based on ceramic material. Their behavior in a liquid (aqueous) medium will depend on their density; in particular, the type/conformation of the mechanical devices holding them in the reaction section will be chosen accordingly.

Reference may be made to the abovementioned patent FR-3 086 670 for an example of a porous material of polyurethane foam type retained by a net system.

According to a first embodiment, the reaction section comprises a reactor, and the support comprises a plurality of layers, successively passed through by the sugary fluid, the portion of spent support and the portion of new and/or regenerated support each corresponding to a layer or a set of adjacent layers of the support.

The support is thus divided into a certain number of portions, in the form of a stack of layers that will successively be passed through by the sugary fluid, and it will be possible to periodically replace one, two or x layers of spent support by the same number layers of new/regenerated support.

Within the meaning of the invention, and very particularly when a support in the form of loose blocks of porous material is chosen, the term "layers" should not be understood in the literal sense as layers which would be perfectly defined relative to one another, continuous and with a planar interface, or which would be perfectly stacked: these layers of material can have uneven, non-planar interfaces, even if they divide the support into portions which are approximately of the same height and/or which contain approximately the same amount of porous material. It is for the sake of clarity that the support is represented in the form of a stack of these "layers".

Advantageously, in this configuration, the portion of spent support and the portion of new and/or regenerated support each correspond to a layer of the support, the portion of spent support withdrawn from the reactor being the furthest upstream layer of the support and the portion of new or regenerated support being introduced into the reactor downstream of the furthest downstream layer of the support.

Throughout the present text, the terms "upstream" and "downstream" are understood as a function of the general direction of flow of the (sugary) fluid in the reaction section, here the reactor, through the support.

According to a variant, the portion/layer of new or regenerated support is introduced in the form of loose blocks of material, into the reactor, in solid form, notably by pneumatic means or mechanical means such as an endless screw.

According to another variant, the portion/layer of new or regenerated support is introduced in the form of loose blocks of material, into the reactor, in a liquid phase, notably in suspension in the sugary fluid supplying the reaction section.

According to a variant, the worn portion/layer of the support is withdrawn from the reactor in the liquid phase. It may notably be withdrawn in suspension in the liquid phase of the fermentation must leaving the reactor.

It is therefore possible to equip the reactor with a specific inlet and/or a specific outlet, dedicated to the replacement of the porous support, or instead to use the existing inlets/outlets for supplying the reactor with sugary fluid and withdrawing the fermentation products therefrom. It should be noted that it is advantageous to provide the outlet for fermentation products (must) with a mechanical means for blocking the solids, of the screen type, so as not to discharge the blocks of porous support unintentionally, (means which will always be present when there is an outlet dedicated to the porous support, which will be removable, so as to be able to remove it/deactivate it when the spent support is to be withdrawal with the stream of fermentation products, during a replacement).

Advantageously, for this first embodiment, the withdrawal of the portion/layer of spent substrate at one of the ends of the substrate and the replacement thereof by a portion/layer of new/regenerated substrate at its opposite end is carried out countercurrent relative to the direction of flow of the (sugary) fluid in the reaction section. The term "countercurrent" is used here since the fluid flows from upstream to downstream, by definition according to the conventions of the present invention, in the reaction section, whereas the support is withdrawn upstream and topped up downstream. This is the most judicious mode of operation since, as explained above, it is generally the furthest upstream portion of the support that tends to become loaded the most/the most quickly with bacteria. The term "ends" is understood here to mean the (upstream/downstream) ends of the support relative to the overall direction of flow of the fluid in the reactor in operation.

Preferably, the sugary fluid passes through the support on which the microorganisms are immobilized in a general direction of flow in the reaction section comprising a reactor, the portion of spent support is withdrawn from the reactor, and the portion of new or regenerated support is introduced as a replacement, the portion of spent support being withdrawn from the reactor in the furthest upstream part of the support and the portion of new or regenerated support being introduced into the reactor in the furthest downstream part of the support.

The portion of spent support that it is preferred to withdrawn from the reactor is the furthest upstream portion of the support, which is also, generally, its most spent portion. And it is preferred to add the portion of new/regenerated support downstream, to take over from the least spent downstream portion: Therefore, a portion of support is not replaced at the same location, a portion of support is withdrawn at one of its ends (the upstream end), and another is added at the other of its ends (the downstream end): Thus the creation of a "gradient" of degree of aging of the support along the direction of flow of the sugary fluid passing through it is created, or at least intensified, the portions/layers of support being more spent the more upstream of the support they are. With this periodic replacement, an "average" degree of ageing of the support is kept substantially constant, and it is possible to extend the production run times and/or, for an equivalent time, to make the run times more productive.

This first embodiment can be implemented in two different ways, with a reactor oriented essentially along a vertical axis:

either with a flow of the sugary fluid in the reactor from top to bottom, the support extending over at least one part of the height of the working volume of the reactor, the portion of spent support being withdrawn from the reactor in the highest part of the support, and the portion of new or regenerated support being introduced into the reactor in the lowest part of the support, or with a flow of the sugary fluid in the reactor from bottom to top, the support extending over at least one part of the height of the working volume of the reactor, the portion of spent support being withdrawn from the reactor in the lowest part of the support, and the portion of new and/or regenerated support being introduced into the reactor in the highest part of the support.

It should be noted that the material of the support will preferably be of low density (PU foam) if a top-down flow of fluid in the reactor is chosen, and that it will preferably be of higher density (ceramic foam) if a bottom-up flow is chosen.

It is of course possible to thus operate a plurality of reactors in parallel, and optionally to pool the collection and treatment of the fermentation musts from each of the reactors.

According to a second embodiment of the invention, the reaction section comprises a series of n reactors fluidically connected in series to one another, and at least one spare reactor. The support is then distributed between the n reactors in the form of n support portions, and a portion of the spent support is periodically replaced by a portion of new or regenerated support by disconnecting a reactor belonging to the series of n reactors in series and containing the portion of spent support and by connecting the spare reactor containing a portion of new or regenerated support to the series of n−1 reactors.

Here, it is therefore the whole of the support contained in a reactor which is the "portion" of support, and it is an entire reactor that is then replaced by another. But the same principle as with the first embodiment is retained, with reactors which will, over the course of the production run, have supports with different degrees of aging from one reactor to another, the reactor the furthest upstream having the "oldest" support.

Preferably, the reactor which is disconnected is the furthest upstream reactor with respect to the general direction of flow of the sugary fluid through the series of n reactors, and the spare reactor which is connected is placed downstream of the furthest downstream reactor of the series with respect to said direction of flow.

As in the case of the first embodiment, there is therefore here a kind of gradient of degree of aging of the support, which decreases from one reactor to the next, from upstream to downstream in the direction of flow of the (sugary) fluid.

According to this second embodiment, there is therefore a series of reactors in production mode, and a series of one or more other reactors, which include the reactor(s) which has/have been disconnected and which will be able to be treated to become operational again in the form of a spare reactor awaiting replacement.

Specifically, once the reactor containing the portion of spent support has been disconnected, various treatments are carried out, generally including draining, and at least one treatment operation for the spent support. This treatment may consist of cleaning, of the type of cleaning with a view to regenerating it, for example according to the procedure described in the abovementioned patent FR-3 086 553, or may consist in replacing it with a new support. Then, optionally, the treatment can be continued by sterilization, in order to store it as a spare reactor.

According to an optional variant, the reaction section comprises at least one reactor which is provided with a fluid recirculation loop, and this being irrespective of the embodiment of the invention (independent reactors or reactors mounted in series). Alternatively or cumulatively, the reaction section comprises at least one reactor provided with mechanical stirring means. The recirculation loop and/or mechanical stirring ensure mixing in the reactor which is equipped therewith, and homogenize(s) the contents.

Irrespective of the embodiment envisaged, the portion of the spent support and the portion of new or regenerated support which replaces it preferably have the same sizing. The overall support is thus kept at a constant size. It should be noted that the porous support may have a certain buoyancy, notably when it is in the form of loose blocks of polyurethane-type polymer foam, which means that if a portion of support is withdrawn at one end of the support and another portion is added at the other end (the case of the first embodiment in particular), with suitable methods of fixing/maintaining the support, after stabilizing the positioning of the portions, the support remains generally in the same place, at the same "height" in the reactor (if the example of a vertically oriented reactor is taken).

Irrespective of the embodiment envisaged, the periodic replacement of the portion of spent support by a portion of new and/or regenerated support can be carried out by withdrawing the portion of spent support from the reaction section and introducing the portion of new and/or regenerated support into the reaction section concurrently, or one after the other.

Preferentially, the portion of new and/or regenerated support is sterilized before introduction into the reaction section.

Irrespective of the embodiment envisaged, the periodic replacement of the portion of spent support by the portion of new or regenerated support is carried out with constant or increasing time intervals, or intervals that decrease with time, or according to time intervals controlled according to a measurement or an evaluation of the degree of deterioration of the support. The degree of deterioration can be evaluated as a function of various indicators: notably the measurement or evaluation of the drop in production performance, the change in the pH, the measurement or evaluation of the change in the ratio between the various products resulting from the fermentation products.

Irrespective of the embodiment envisaged, the process continues, preferably, to produce during the periodic replacement of a portion of spent support by a portion of new or regenerated support:

in the first embodiment, this continuous replacement is facilitated if, as already mentioned, the new support is introduced with the supply of sugary stream and the spent support is withdrawn with the stream of products leaving the reactor, in the second embodiment, the replacement of one reactor by another may lead to a short interruption in production, the time for disconnecting one reactor and for reconnecting the other.

In either embodiment, this partial replacement of support leads to a better smoothing of the production.

The invention, in its preferred application, aims to produce a fermentation must comprising isopropanol, butanol and ethanol, the microorganisms being derived from a strain belonging to the genus *Clostridium*. Preferably, they are supported by a porous support of the foam type based on polymer material, such as polyurethane, or on ceramic materials.

According to a preferred embodiment of the invention, the process according to the present invention relates to the production of a mixture of alcohols of ABE or IBE or IBEA type, according to which process a sugary fluid is introduced into a section reaction comprising a support made of porous solid material on which microorganisms of the genus *Clostridium* are immobilized, said support comprising a plurality of portions or layers of loose porous solid material, which are arranged successively in a general direction of flow of said sugary fluid. This preferred embodiment also relates to the reaction section thus equipped with a support.

The invention will be described below in greater detail with the aid of non-limiting implementation examples.

LIST OF THE FIGURES

All the figures are highly schematic, only the elements/devices that are most significant in view of the invention are shown, and, in particular, all the pipes, valves, etc. are not shown. The scale is not necessarily respected, and the references that are identical from one figure to another correspond to the same element, to the same stream, etc. All the reactors used are of cylindrical type with a vertical longitudinal axis.

DESCRIPTION OF THE EMBODIMENTS

The Fermentation Process of the Invention According to a First Embodiment

A first embodiment is described with the aid of FIGS. 1 to 4. The reactors 1 of FIGS. 1 to 4 are identical, apart from the fluid inlets/outlets which are configured differently. These are conventional fermentation reactors, essentially of cylindrical shape, which are oriented along a vertical axis.

9

Figure 1:
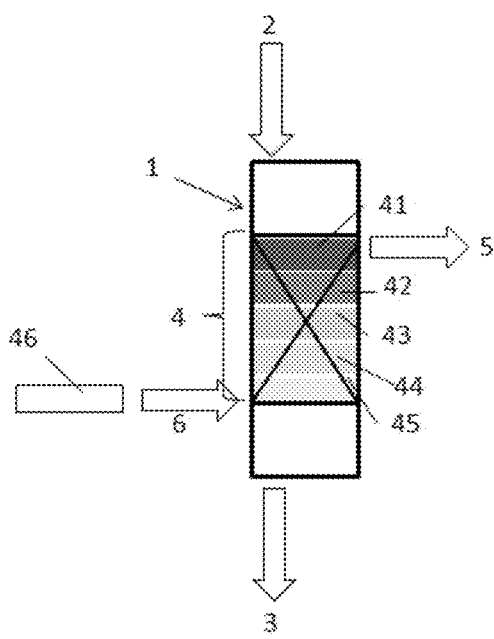
FIG. 1 shows an example of a process according to the first embodiment of the invention.
Figure 2:
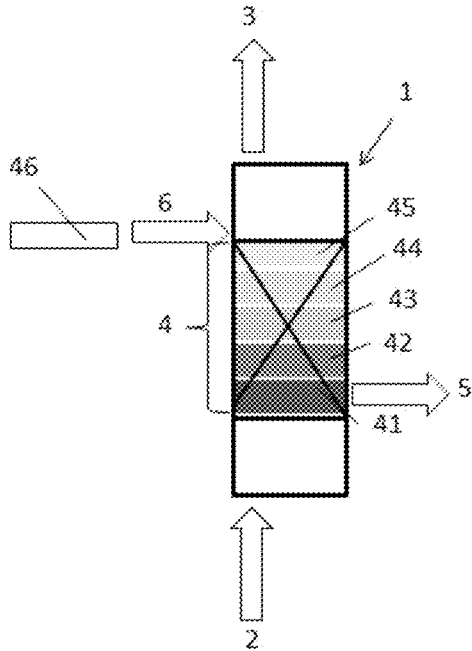
FIG. 2 shows a process according to another example of a process according to the first embodiment of the invention represented in FIG. 1.

FIGS. 1 and 2 are first of all described: the reactors 1 are supplied with a sugary fluid 2 and a stream of fermentation must 3 is withdrawn therefrom. In the variant of FIG. 1, the reactor 1 is supplied in the top part of the reactor, and the must 3 is extracted in the bottom part of the reactor 1: the flow stream in the reactor is referred to as "downflow". In the variant of FIG. 2, it is the reverse, it is then referred to as "upflow" in the reactor 1.

The sugary fluid 2 comprises C5 and/or C6 sugars in the aqueous phase. The fermentation must (which can also be referred to as fermentation liquor or wine or fermentation products) 3 is itself enriched in isopropanol, butanol, ethanol and acetone compared to the sugary fluid 2 by conversion of the sugars into alcohol/solvent under the action of a micro-organism deposited on the solid support 4 contained in the reactor 1. This support 4 comprises a polyurethane foam, which acts as a moving bed in the reactor 1 in the form of blocks arranged loose and retained by systems of screens/nets, not shown, which hold them in place over a certain height in the reactor, like a fixed bed. (Alternatively, the foam blocks can be arranged in a structured manner, not loose). The microorganism colonizing the support is of *Clostridium* type.

The fermentation step in the fermentation reactor 1 may be performed at a temperature of between 28° C. and 40° C., preferably between 30° C. and 37° C., so that the fermentation must 3, 3' comprises fermentation reaction products of IBEA type, for example isopropanol, which is then discharged from the reactor.

Next, the fermentation must 3 (steps not shown) is treated, notably with one or more successive separation-type steps: it is for example introduced into a separation unit making it possible to separate and extract the compounds of interest from the fermentation must, the latter being discharged in order to be converted or upgraded as is. The residues from the separation, commonly referred to as vinasses, are discharged from the separation unit; they are generally composed of water and also of any liquid or solid product not converted or extracted during the preceding steps. The separation unit may carry out one or more distillations, and optionally a separation of the solid matter and/or the suspended matter, for example by centrifugation, decantation and/or filtration.

Returning to reactor 1: the support 4 is therefore used to immobilize the microorganisms (hereinafter also referred to by the terms bacteria or bacterial biomass), and to promote their growth by adsorption on solid support 4 directly in fermentation reactor 1. This immobilization/adsorption step can also be carried out indirectly, in a secondary tank not shown (optional), operating for example in "in stream" mode with respect to the fermentation reactor 1: The solid support 4, once loaded with bacterial biomass, is then introduced into the fermentation reactor 1.

The solid support 4 is partially or, preferably, completely immersed, when the reactor 1 is in operation, in particular to increase the formation of the biofilms and improve the performance.

The solid support has a shape suitable for implementing the process of the invention, that is to say it consists of a plurality of layers stacked on top of each other in the vertical axis of the reactor, which is also the general flow axis of the fluid passing through the reactor. The layers are designed to be able to be removed from/added to in the reactor independently of the others. In FIGS. 1 and 2, five layers 41 to 45 have been shown, all of the same size, in particular of the same height measured along the vertical axis, and all contiguous. This is a simple embodiment example, the invention adapting the size and the number of layers depending, in particular on the size of the reactor, and the layers can be superimposed on each other without necessarily being in contact with each other, it being possible for a space to be provided between two consecutive layers of the stack.

As indicated above, the support 4 here consists of a stack of loose foam blocks. The "layers" should not therefore be understood in the literal sense, do not have a planar interface, do make it possible to "cut" the support into portions of approximately the same size, here of the same height or, which amounts to the same thing, into portions containing the same amount of foam, these portions being "stacked" along the longitudinal axis, here the vertical axis, of the reactor.

The foam blocks can be in the form of cubes or parallelepipeds or other elements of any three-dimensional shape. The net or the meshed container 10 of screen type can define a shape of cylindrical type, the diameter of which is less than or substantially equal to the internal diameter of the fermentation reactor 1. More generally, the layers can have a cross section of the same geometric shape (circular or non-circular) and slightly smaller than that of the reactor, whether cylindrical or non-cylindrical. Within each layer, the particles or blocks of foam can move, they are mobile but contained by the net/screen-type container.

The solid support layers 41 to 45 are preferably centered with respect to the internal walls of the fermentation reactor 1. Advantageously, they do not disrupt the circulation of the liquid at the inlet or at the outlet of the reactor, notably when it is operated continuously. Furthermore, the possible presence of insoluble materials such as those derived from the major cereal plants does not pose any problems. The stream of sugary fluid arriving via line 1 may also be introduced at the level of the layers of solid support 4, for example when the first layer or layers are flush with the surface of the reaction medium of the fermentation reactor 1. Advantageously, when the solid support is flush with the surface of the reaction medium at the level of the inlet of the sugary fluid, the medium is locally less concentrated in alcohol and growth of the bacteria is promoted.

The various layers 41 to 45 are represented symbolically with a shade of gray that is stronger the more spent the foam that they contain is, that is to say the higher the "age" of the foam in the production run of the reactor. As seen in FIGS. 1 and 2, it is in the furthest upstream part of the support 4 that the layers are the most spent/oldest: the more upstream the position of the layer, the older/more spent it is. The deterioration actually starts with the colonization of the support. Eventually, the pores become clogged or the bacteria die and no longer produce or produce less, and this phenomenon is greatest in the furthest upstream zone, which receives the sugary fluid first.

The process according to the invention consists in replacing the most spent (furthest upstream) layer 41 by extracting it from the reactor (arrow 5), then by replacing it with a new or regenerated layer 46 (arrow 6). (This layer has been represented symbolically in the figure before it is introduced into the reactor, insofar as it is preferred to add the support in the form of loose foam blocks: before it is introduced, the support can be stored and transported to the reactor in a container of any shape, naturally). Generally, the height of the support 4 in the reactor after this replacement remains unchanged. After the replacement, it is layer 42 that becomes the oldest/most spent layer in the stack of layers, and layer 46 which becomes the "youngest". This layer is preferably bare, it contains only polyurethane foam, and it will gradually become activated by bacterial contamination from the other layers and it too will grow biofilms on the surface of the foam.

As shown schematically in FIGS. 1 and 2, the replacement can be carried out via dedicated inlets/outlets made in the side wall of the reactor: To withdraw the spent foam, a dedicated outlet can be provided, the discharged foam then being separated from the fluid it has entrained, the fluid optionally being reinjected into the reactor. To introduce the new or regenerated foam, use may be made of pneumatic means or mechanical means of the endless screw type.

It was possible to verify that with such a partial replacement at suitable time frequencies depending on the targeted production run time, this countercurrent system (between the circulation of the fluid in the reactor and the partial support change) is very advantageous since it makes it possible to keep the productivity virtually constant over time during the production run, and to increase the working time of the reactor (or to keep it constant with a better productivity).

Figure 3:
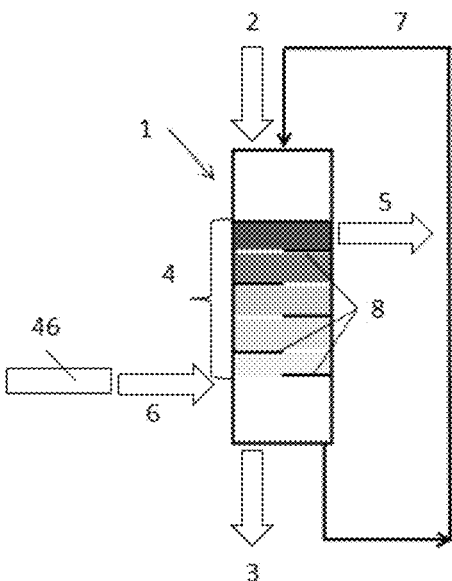
FIG. 3 shows a variant of the process represented in FIG. 1.

The process from FIG. 3 is a variant of the process from FIG. 1: all other things being equal:

firstly, a recirculation loop 7 is added to the reactor, which makes it possible to better homogenize the contents of the reactor and to create favorable mixing/circulation in the reactor, secondly, deflectors 8 in the form of screens, perforated plates, solid plates or equivalent means are added, which are arranged alternately, in steps, over the height of the support, the spacing between two successive deflectors measured along the height of the reactor, defining the height of a support layer within the meaning of the invention. Here, mechanical means are therefore used to identify the layers and to direct the path of the fluid through the support 4 (in particular in the case of solid, non-perforated plates).

Figure 4:
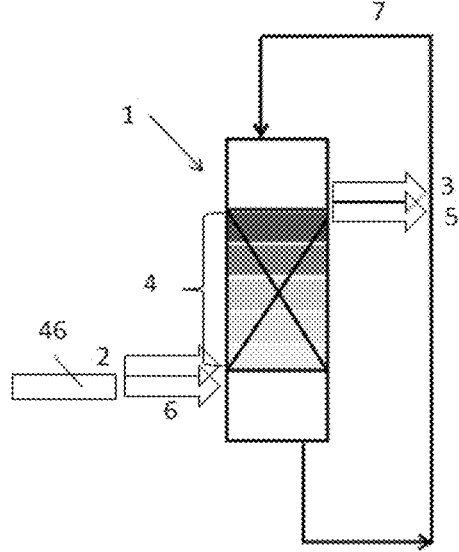
FIG. 4 shows a variant of the process represented in FIG. 1.

The process from FIG. 4 is another variant of FIG. 1. The differences from FIG. 1 are as follows:

firstly, as in the variant from FIG. 3, a recirculation loop is provided, secondly, dedicated inlets/outlets for the foam are not used. Indeed, here, the sugary fluid is introduced into the bottom part of the reactor via a sugary fluid feed inlet, which is also used to periodically introduce new foam. To do this, blocks of foam in suspension are briefly added to the sugary fluid. Either the foam is added to the sugary fluid upstream, prior to its introduction into the reactor, or the sugary fluid and the foam are jointly introduced directly into the reactor feed inlet. For the withdrawal of the spent foam, in the top part, a controlled portion of foam is removed with the must 3 via the must withdrawal outlet, for example by providing the outlet with a screen sized to retain the blocks of foam, which screen is removed when the spent foam is withdrawn.

The Fermentation Process of the Invention
According to a Second Embodiment

Figure 5:
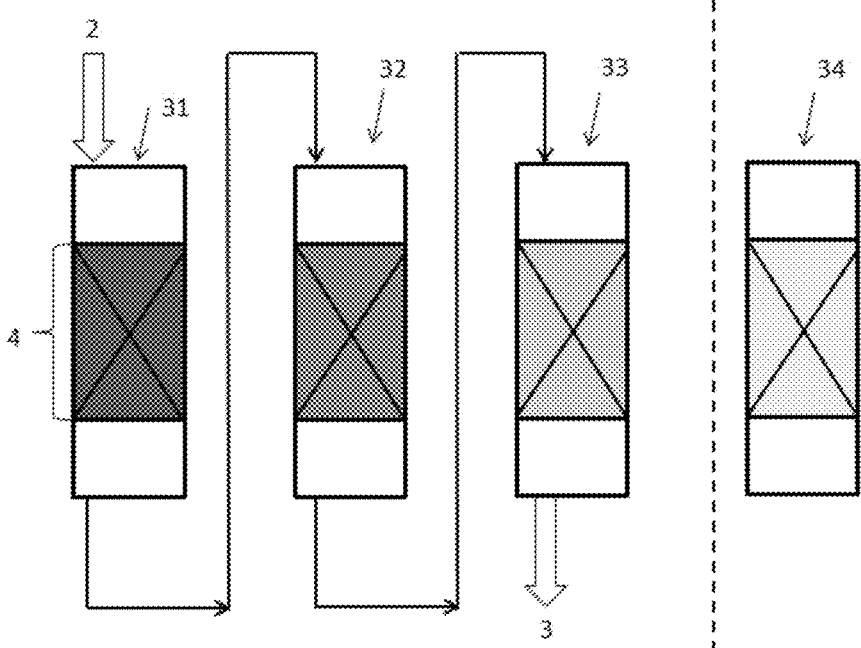
FIG. 5 shows a process according to a second embodiment of the invention, in production phase.
Figure 6:
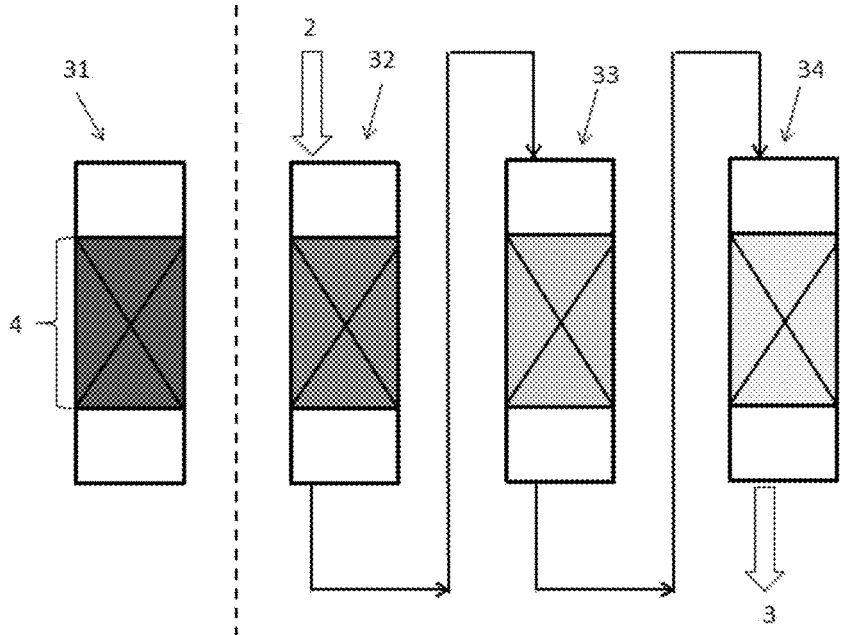
FIG. 6 shows the process according to the second embodiment of the invention according to FIG. 5, during the phase of partial replacement of the support of the microorganisms.

This second embodiment is illustrated in FIGS. 5 and 6. Use is made of a series of three fermentation reactors 31, 32, 33 mounted in series with the appropriate fluidic connections. Of course, this is just one example, and the series of reactors can include more reactors. As in the previous embodiment, the reactors, which are all identical, are of the cylindrical type and are oriented vertically. Here they are all downflow reactors. The sugary fluid 2 is introduced into the top part of the first reactor 31, the furthest upstream in the series of three. The fermentation must 3 exits at the bottom part of the last reactor 33 of the series, the furthest downstream. A fourth reactor 34, identical to the other three, is the inactive, spare reactor.

All four reactors are provided with a support 4 consisting of blocks of polyurethane foam as previously, held in position in each of the reactors by a container of the net or screen(s) type. The supports 4 of the reactors have different ages, the more upstream the reactor they are arranged in, the older/more spent they are. It is in this way that the support of the reactor 31 has, for example, 1500 production operating hours, the support of the reactor 32 has 1000 operating hours, and the support of the reactor 33 has only 500 operating hours. Every 500 hours, the reactor having the most spent support, here the reactor 31 therefore, will be disconnected from the rest of the series of reactors, and the spare reactor 34 will be connected, downstream of the downstream reactor 33. Naturally, the appropriate modifications are made: the sugary fluid is redirected to the inlet in the top part of the reactor 32, and the must leaving the reactor 33 is redirected to the inlet in the top part of the reactor 34, from which, in the bottom part, the final must leaves.

The reactor 31 which has been disconnected is drained and cleaned. Its aged support 4 is replaced by a support with new and/or regenerated foam. It is then sterilized and put on hold, to constitute a spare reactor. It is possible to operate with a spare reactor always ready, and at least one disconnected reactor being cleaned/prepared.

The colonization of the newly used reactor 34 is favored by the arrival of liquid heavily loaded with biomass originating from the preceding reactors. Each reactor can have its own recirculation loop (not shown). Several series of reactors can be used in parallel, for a common collection of fermentation musts in order to pool the treatment thereof.

Here too, it is verified that with this replacement of reactors, it is possible to increase the production run times and/or improve the productivity of the process.

DESCRIPTION OF THE EMBODIMENTS

The Sugary Fluid

According to one or more embodiments, the sugary fluid comprises an aqueous solution of C5 and/or C6 sugars obtained from lignocellulose, and/or of sugars obtained from sugar-producing plants (for example, glucose, fructose and sucrose), and/or of sugars obtained from starchy plants (for example, dextrins, maltose and other oligomers, or even starch). According to one or more embodiments, the aqueous solution of C5 and/or C6 sugars originates from the treatment of a renewable source. According to one or more embodiments, the renewable source is of the lignocellulosic biomass type which may notably comprise ligneous substrates (for example, deciduous plants and coniferous plants), agricultural byproducts (for example, straw) or byproducts from industries generating lignocellulosic waste (originating from agrifood or paper industries). The renewable source may also originate from sugar-producing plants, for instance sugar beet and sugarcane, or from starchy plants such as corn and wheat. The aqueous solution of C5 and/or C6 sugars may also originate from a mixture of various renewable sources.

The Biomass Produced by the Strain Belonging to the Genus *Clostridium*

The bacterial biomass is mainly adsorbed in the form of a biofilm onto a solid support. Preferably, the bacteria are strains belonging to the species *Clostridium beijerinckii* and/or *Clostridium acetobutylicum*. The bacteria used in the process may be strains which may or may not be genetically modified and which naturally produce isopropanol and/or *Clostridium* strains which naturally produce acetone and which are genetically modified to make them produce isopropanol. In the following examples, it is *Clostridium beijerinckii* DSM 6423.

The Solid Support

The solid support comprises a polyurethane foam. Polyurethane foam is particularly advantageous since it allows access not only to the production of mixtures of IBEA type, but also allows access to production of continuous type by immobilization of the bacterial biomass. Specifically, the polyurethane foam is capable of fixing bacteria of the genus *Clostridium* in a sufficiently substantial manner (i.e. beyond the dilution rate causing cell wash-out) making it possible to continuously produce mixtures of IBEA type. Furthermore, polyurethane foam is suitable for immobilization by immersion in a reactor. Alternatively, a foam based on ceramic material(s) can be used.

According to one or more embodiments, the polyurethane foam has:
- volume cavities (i.e. pores or cells) whose equivalent sphere diameter is between 0.1 and 5 mm, preferably between 0.25 mm and 1.1 mm, preferably between 0.55 and 0.99 mm, and/or
- an apparent density (i.e. apparent mass per unit volume) measured in air of between 10 and 90 g/L, preferably between 10 and 80 g/L, preferably between 15 and 45 g/L, such as between 20 and 45 g/L or between 25 and 45 g/L.

It is possible to use a solid support 4 of a single block in the second embodiment illustrated in FIGS. 5 and 6. For the first embodiment illustrated in FIGS. 1 to 4, it is possible to use blocks (for example in the form of disks) which are stacked. Preferably, however, the solid support comprises a net or a meshed container comprising cubes or parallelepipeds or other elements of any three-dimensional shape (e.g. polyhedra) of large or small size (at least one dimension between 3 mm and 10 m, such as from 2 cm to 1 m), and the net or the meshed container forming a cylinder, the diameter of which is less than or substantially equal to the internal diameter of the fermentation reactor 1. It may be that gas emissions tend to cause the solid support 4 to rise: at least one perforated plate, a simple net or at least one screen may suffice to keep the solid support 4, which is for example in motion, in the fermentation reactor 1.

The Operating Conditions Preferred According to the Invention, and Used in the Examples The temperature in the reactor(s) is between 28° C. and 40° C., preferably between 30° C. and 37° C., in particular here 36° C.

The pressure in the reactor(s) is substantially atmospheric pressure (plus the pressure head of water in the reactor(s))

The concentration of sugary fluid is between 65 and 35 g/L, preferably between 40 and 60 g/L, and in particular here 44 g/L (aqueous medium)

The reactor(s) are operated continuously, with imposed dilution rates

The targeted fermentation yield is between 0.28 g and 0.34 g of IBEA product/g of sugar used, and in particular here 0.31 g of IBEA product/g of sugar used.

The microorganism is *Clostridium beijerinckii* DSM 6423

The porous support 4 is PU foam in the form of small loose parallelepipeds of dimensions 20 mm×20 mm×7 mm (but, as indicated above, may have other dimensions, for example smaller dimensions such as: 5 mm×5 mm×3 mm or 10 mm×10 mm×7 mm, or larger dimensions)

For all the following examples, a plant of 8 fermentation reactors defining a working volume of 400 m³ each is considered.

Example 1 (Comparative)

The 8 fermentation reactors are filled with solid support 4 and each operate for a given production run, here of 1500 hours. Then they are all drained, cleaned and sterilized. They are then filled again with support for a new production run of 1500 hours.

The reactors are sequenced (they are made to operate in a time-staggered manner) so as to have a generally continuous production downstream. Buffer tanks are also provided downstream of the reactors to smooth the flow rates for the downstream section.

For a given reactor, it is assumed that the following productivity profile p is followed:
- ramp-up: from 0 to 500 h, increase from 0 g/L·h to 2 g/L·h
- production: from 0 to 1500 h, constant productivity of 2 g/L·h The time needed to drain/clean/sterilize/refill a reactor is 150 hours. Each reactor operates for 1500 hours, according to the productivity profile described above. This profile is equivalent to a constant apparent productivity of 1.67 g/L·h over 1500 h.

For 150 hours plus 1500 hours, i.e. a total of 1650 hours, a reactor produces the following amount P1 of alcohols:

$P1=1.67*1E-6*400*1000*1500=1000$ t, i.e. 1000 tonnes of alcohols.

A reactor performs over one year, i.e. 8000 hours, 8000/1650 production cycles, i.e. 4.85 cycles, and thus produces 4850 tonnes of alcohols.

The time lag T of the reactors is calculated, which is equal to the draining time plus the cleaning time plus the sterilization time plus the refilling time plus the maximum operating time divided by the number of reactors −1, i.e.:

$$T1=(150+1500)/7=235.7 \text{ h}$$

Thus, at any moment, seven reactors are in operation and one is being cleaned. 33 950 tons of alcohols are then produced in one year.

Example 2 (According to the Invention)

This implements the first embodiment of the invention according to FIG. 1 (it would apply analogously to the variants according to one of FIGS. 2 to 4).

With this example, the support is continuously renewed in each of the 8 reactors. Each reactor can thus operate for up to 3000 hours, or even 5000 hours, before cleaning.

For a production of 5000 hours, the productivity profile becomes:
- ramp-up: from 0 to 500 h, increase from 0 g/L·h to 2 g/L·h
- production: from 0 to 5000 h, constant productivity of 2 g/L·h This profile is equivalent to a constant apparent productivity p of 1.90 g/L·h over 5000 h.

For 150 hours plus 5000 hours, i.e. 5150 hours, a reactor produces the following amount P2 of alcohols: $P2=1.9*1E-6*400*1000*5000=3800$ t, i.e. 3800 tonnes of alcohol.

A reactor performs over one year, i.e. 8000 hours, 8000/5150, i.e. 1.56 production cycles, and thus produces 5903 tonnes of alcohols.

The time lag T2 of the reactors is calculated, which is equal to the draining time plus the cleaning time plus the sterilization time plus the refilling time plus the maximum operating time, divided by the number of reactors −1:

$$T2 = (150+5000)/7 = 735.7 \text{ h.}$$

Thus, at any moment, seven reactors are in operation and one is being cleaned. 41 320 tonnes of alcohols are then produced in one year, i.e. a 21.7% increase in production compared to example 1, which is a very significant increase.

Example 3 (According to the Invention)

This implements the second embodiment of the invention illustrated by FIGS. 5 and 6.

For a given reactor, it is assumed that the following productivity profile is followed:

ramp-up: from 0 to 500 h, increase from 0 g/L·h to 2 g/L·h production: from 0 to 1500 h, constant productivity of 2 g/L·h The time needed to drain/clean/sterilize/refill a reactor is 150 hours.

The time lag T3 of the reactors is calculated, which is equal to the maximum operating time, divided by the number of reactors:

$$T3 = 1500/8 = 187.5 \text{ h.}$$

A reactor performs over one year, i.e. 8000 hours, 8000/1500 production cycles, i.e. 5.33 cycles. Each of the 8 reactors R1 to R8 has a different age T according to table 1 below, "0" meaning "being cleaned" etc.:

TABLE 1

| T (h) | 0 | 187.5 | 375 | 562.5 | 750 | 937.5 | 1125 | 1312.5 | 1500 |
|---|---|---|---|---|---|---|---|---|---|
| R1 age (h) | 1500 | 0 | 187.5 | 375 | 562.5 | 750 | 937.5 | 1125 | 1312.5 |
| R2 age (h) | 1312.5 | 1500 | 0 | 187.5 | 375 | 562.5 | 750 | 937.5 | 1125 |
| R3 age (h) | 1125 | 1312.5 | 1500 | 0 | 187.5 | 375 | 562.5 | 750 | 937.5 |
| R4 age (h) | 937.5 | 1125 | 1312.5 | 1500 | 0 | 187.5 | 375 | 562.5 | 750 |
| R5 age (h) | 750 | 937.5 | 1125 | 1312.5 | 1500 | 0 | 187.5 | 375 | 562.5 |
| R6 age (h) | 562.5 | 750 | 937.5 | 1125 | 1312.5 | 1500 | 0 | 187.5 | 375 |
| R7 age (h) | 375 | 562.5 | 750 | 937.5 | 1125 | 1312.5 | 1500 | 0 | 187.5 |
| R8 age (h) | 187.5 | 375 | 562.5 | 750 | 937.5 | 1125 | 1312.5 | 1500 | 0 |

Each of the 8 reactors has a different productivity p, according to table 2 below:

TABLE 2

| T (h) | 0 | 187.5 | 375 | 562.5 | 750 | 937.5 | 1125 | 1312.5 | 1500 |
|---|---|---|---|---|---|---|---|---|---|
| p R1 (g/L · h) | 0 | 2 | 2 | 2 | 2 | 2 | 0.75 | 0.25 | 0 |
| p R2 | 0.25 | 0 | 2 | 2 | 2 | 2 | 2 | 0.75 | 0.25 |
| p R3 | 0.75 | 0.25 | 0 | 2 | 2 | 2 | 2 | 2 | 0.75 |
| p R4 | 2 | 0.75 | 0.25 | 0 | 2 | 2 | 2 | 2 | 2 |
| p R5 | 2 | 2 | 0.75 | 0.25 | 0 | 2 | 2 | 2 | 2 |
| p R6 | 2 | 2 | 2 | 0.75 | 0.25 | 0 | 2 | 2 | 2 |
| p R7 | 2 | 2 | 2 | 2 | 0.75 | 0.25 | 0 | 2 | 2 |
| p R8 | 2 | 2 | 2 | 2 | 2 | 0.75 | 0.25 | 0 | 2 |

It is then possible to calculate the production P, expressed by weight in kg, of the 8 reactors, according to table 3 below: (it should be noted that each box of this table indicates the production over the 187.5 hour time interval considered, and not the cumulative production since time T=0.)

TABLE 3

| P (kg) | 0 | 187.5 | 375 | 562.5 | 750 | 937.5 | 1125 | 1312.5 | 1500 |
|---|---|---|---|---|---|---|---|---|---|
| R1 | | 150000 | 150000 | 150000 | 150000 | 150000 | 56250 | 18750 | 0 |
| R2 | | 0 | 150000 | 150000 | 150000 | 150000 | 150000 | 56250 | 18750 |
| R3 | | 18750 | 0 | 150000 | 150000 | 150000 | 150000 | 150000 | 56250 |
| R4 | | 56250 | 18750 | 0 | 150000 | 150000 | 150000 | 150000 | 150000 |
| R5 | | 150000 | 56250 | 18750 | 0 | 150000 | 150000 | 150000 | 150000 |
| R6 | | 150000 | 150000 | 56250 | 18750 | 0 | 150000 | 150000 | 150000 |
| R7 | | 150000 | 150000 | 150000 | 56250 | 18750 | 0 | 150000 | 150000 |
| R8 | | 150000 | 150000 | 150000 | 150000 | 56250 | 18750 | 0 | 150000 |
| TOTAL | | 825000 | 825000 | 825000 | 825000 | 825000 | 825000 | 825000 | 825000 |
| | | | | | | | | | 6600000 kg |

Therefore, 6 600 000 kg, i.e. 6600 tonnes, of alcohols are produced per production cycle. With 5.33 production cycles per year, 35 200 tonnes/year of alcohols are therefore produced with this technology, which corresponds to an increase in production of 3.7% compared to the results of example 1, which is not inconsiderable.

In conclusion, with the partial renewal of the immobilization support during production, with support portions of different ages, different plant configurations can be adopted, either with one (or more) countercurrent moving-bed reactors (embodiment 1), or with a sequence of simulated moving-bed reactors (embodiment 2). Whether according to the first or the second embodiment, the invention makes it possible to increase the production, for an equivalent number of reactors.

Each configuration also has advantages that are specific thereto: the first embodiment is the most economical to implement, and the one that offers the greatest increase in production, while the second embodiment has, for its part, an industrial implementation that is probably easier.

The invention claimed is:

1. A process for producing alcohols, characterized in that it is a process for producing a mixture of alcohols of Acetone-Butanol-Ethanol type, Isopropanol-Butanol-Ethanol type, or Isopropanol-Butanol-Ethanol-Acetone type, according to which a sugary fluid (2) is introduced into a reaction section (1) comprising a support made of porous solid material and comprising a plurality of portions or layers of loose porous solid material, which are arranged successively in a general direction of flow of said sugary fluid (2) in the reaction section (1), (4) on which microorganisms of the genus *Clostridium*, which microorganisms produce isopropanol naturally, are genetically modified to produce isopropanol, or both, are immobilized, in order to produce, by fermentation, an alcohol-enriched must (3) under the action of said microorganisms, characterized in that the process is carried out continuously, in that a portion of spent support (41) is periodically replaced by a portion of new support, by a portion of regenerated support, or by a portion of a combination of new support and regenerated support (46), characterized in that only a portion is replaced each time a replacement is made.

2. The process as claimed in claim 1, characterized in that the microorganisms are immobilized in the form of biofilms or aggregates on the support (4).

3. The process as claimed in claim 1, characterized in that said plurality of support portions have a decreasing degree of deterioration from upstream to downstream.

4. The process as claimed in claim 1, characterized in that the portion of spent support (41) which is furthest upstream in the support (4) is replaced by the portion of new support, by the portion of regenerated support, or by the portion of the combination of new support and regenerated support (46) which is placed downstream of the furthest downstream portion of the support.

5. The process as claimed in claim 1, characterized in that the support (4) comprises loose blocks of porous solid material immersed in a liquid reaction medium bathing the reaction section, and which are held in the reaction section by mechanical devices, which are meshed or are in the form of deflectors (8).

6. The process as claimed in claim 1, characterized in that the reaction section comprises a reactor (1), and in that the support comprises a plurality of layers (41, 42, 43, 44, 45), successively passed through by the sugary fluid (2), the portion of spent support (41) and the portion of new support, the portion of regenerated support, or the portion of a combination of new support and regenerated support (46) each corresponding to a layer of the support, the portion of spent support withdrawn from the reactor being the furthest upstream layer of the support and the portion of new support, the portion of regenerated support, or the portion of a combination of new support and regenerated support being introduced into the reactor downstream of the furthest downstream layer of the support.

7. The process as claimed in claim 1, characterized in that the portion or layer of new support, by a portion of regenerated support, or by a portion of a combination of new support and regenerated support (46) is introduced in the form of loose blocks of material, into the reactor, in solid form or in a liquid phase.

8. The process as claimed in claim 6, characterized in that the spent portion or layer of the support (41) is withdrawn from the reactor in the liquid phase, notably in suspension in the liquid phase of the fermentation must leaving the reactor.

9. The process as claimed in claim 6, characterized in that the withdrawal of the portion or layer of spent substrate (41) at one of its ends, and the replacement thereof by a portion or layer of new support, by a portion of regenerated support, or by a portion of a combination of new support and regenerated support (46) at its opposite end is carried out counter current relative to the direction of flow of the sugary fluid (2) in the reaction section.

10. The process as claimed in claim 6, characterized in that the reactor (1) is oriented essentially vertically, with:

either a flow of the sugary fluid (2) in the reactor from top to bottom, and the support (4) extending over at least one part of the height of the working volume of the reactor, the portion of spent support (41) being withdrawn from the reactor in the highest part of the support, and the portion of new support, by the portion of regenerated support, or by the portion of the combination of new support and regenerated support (46) being introduced into the reactor in the lowest part of the support, or a flow of the sugary fluid (2) in the reactor from bottom to top, and the support extending over at least one part of the height of the working volume of the reactor, the portion of spent support (41) being withdrawn from the reactor in the lowest part of the support, and the portion of new support, by the portion of regenerated support, or by the portion of the combination of new support and regenerated support (46) being introduced into the reactor in the highest part of the support.

11. The process as claimed in claim 1, characterized in that the reaction section comprises a series of n reactors (31, 32, 33) fluidically connected in series to one another, and at least one spare reactor (34), the support (4) being distributed between the n reactors in the form of n support portions, and in that a portion of the spent support is periodically replaced by a portion of new or regenerated support by disconnecting a reactor (31) belonging to the series of n reactors in series and containing the portion of spent support and by connecting the spare reactor (34) containing a portion of new or regenerated support to the series of n–1 reactors.

12. The process as claimed in claim 11, characterized in that the reactor (31) which is disconnected is the furthest upstream reactor with respect to the general direction of flow of the sugary fluid (2) through the series of n reactors, and in that the spare reactor (34) which is connected is placed downstream of the furthest downstream reactor (33) of the series with respect to said direction of flow.

13. The process as claimed in claim 11, characterized in that once the reactor (31) containing the portion of spent support has been disconnected, the reactor is drained and at least one operation is performed for treating the spent support, at least one of the at least one operation comprising regenerating the spent support or replacing the spent support with a new support.

14. The process as claimed in claim 1, characterized in that the reaction section comprises at least one reactor (1) which is provided with a fluid recirculation loop (7).

15. The process as claimed in claim 1, characterized in that the periodic replacement of the portion of spent support (41) by the portion of new support, by the portion of regenerated support, or by the portion of the combination of new support and regenerated support (46) is carried out with constant or increasing time intervals, or intervals that decrease with time, or according to time intervals controlled according to a measurement or an evaluation of the degree of deterioration of the support.

16. The process as claimed in claim 1, characterized in that a fermentation must is produced comprising isopropanol, butanol and ethanol.

17. The process as claimed in claim 5, characterized in that the meshed mechanical devices are selected from screens and nets.

18. The process as claimed in claim 5, characterized in that the loose blocks of porous solid material are based on polymer foam or ceramic material foam.

19. The process as claimed in claim 7, characterized in that the portion or layer of new support, by a portion of regenerated support, or by a portion of a combination of new support and regenerated support (46) is introduced in the form of loose blocks of material, into the reactor, in solid form via endless screw, or in a liquid phase-in suspension in the sugary fluid supplying the reaction section.

20. The process as claimed in claim 13, characterized in that the reactor (31) is sterilized and is stored as a spare reactor.

* * * * *